(12) United States Patent
Meller

(10) Patent No.: US 7,050,167 B2
(45) Date of Patent: May 23, 2006

(54) NEPHELOMETRIC DETECTION UNIT WITH OPTICAL IN-PROCESS CONTROL

(75) Inventor: Paul Meller, Wehrheim (DE)

(73) Assignee: Dade Behring Marburg GmbH, Marburg (DE)

(*) Notice: Subject to any disclaimer, the term of this patent is extended or adjusted under 35 U.S.C. 154(b) by 0 days.

(21) Appl. No.: 10/717,594

(22) Filed: Nov. 19, 2003

(65) Prior Publication Data

US 2004/0075838 A1 Apr. 22, 2004

Related U.S. Application Data

(63) Continuation of application No. 09/428,496, filed on Oct. 28, 1999, now abandoned.

(30) Foreign Application Priority Data

Oct. 28, 1998 (DE) ................. 198 49 597

(51) Int. Cl.
*G01N 21/51* (2006.01)
(52) U.S. Cl. ..................................... 356/338
(58) Field of Classification Search ........ 356/336–343; 250/574
See application file for complete search history.

(56) References Cited

U.S. PATENT DOCUMENTS

| | | | |
|---|---|---|---|
| 3,310,680 A | | 3/1967 | Hasegawa |
| 3,786,261 A | * | 1/1974 | Tucker ....................... 250/205 |
| 3,787,124 A | * | 1/1974 | Lowy et al. ................ 356/434 |
| 3,804,535 A | * | 4/1974 | Rodriguez .................. 356/217 |
| 4,343,552 A | | 8/1982 | Blades |
| 4,348,111 A | * | 9/1982 | Goulas et al. .............. 356/336 |
| 4,482,247 A | * | 11/1984 | Meltz et al. ................ 356/343 |
| 4,549,809 A | * | 10/1985 | Minekane et al. .......... 356/436 |
| 4,730,922 A | | 3/1988 | Bach et al. |
| 4,842,406 A | | 6/1989 | Von Bargen |
| 5,262,841 A | * | 11/1993 | Blesener et al. ............ 356/338 |
| 5,298,968 A | * | 3/1994 | Cheung ...................... 356/338 |

FOREIGN PATENT DOCUMENTS

| | | |
|---|---|---|
| DE | 1 296 828 | 6/1969 |
| DE | 3630292 C1 | 2/1988 |

* cited by examiner

*Primary Examiner*—Richard A. Rosenberger
(74) *Attorney, Agent, or Firm*—Finnegan, Henderson, Farabow, Garrett and Dunner, L.L.P.

(57) ABSTRACT

The present invention relates to the field of the use of automated measurement systems in analysis and in in-vitro diagnosis. In particular, the apparatus described enables automatic quality control and validation of characteristic process engineering parameters, in particular characteristic optical parameters, during the measurement of scattered light signals.

27 Claims, 3 Drawing Sheets

NEPHELOMETRIC DETECTION UNIT WITH OPTICAL IN-PROCESS CONTROL

CROSS-REFERENCE TO RELATED APPLICATIONS

This is a continuation of application Ser. No. 09/428,496, filed Oct. 28, 1999, now abandoned, which claims the right to priority based on German Patent Application No. 198 49 597.8, filed Oct. 28, 1998, all of which are incorporated herein by reference.

BACKGROUND OF THE INVENTION

1. Field of the Invention

The present invention relates to the filed of automated measurement systems for use in analysis and in in-vitro diagnosis. In particular, the apparatus described enables automatic quality control and validation of characteristic process engineering parameters, in particular characteristic optical parameters, during the measurement of scattered light signals.

2. Description of the Related Art

An increasing demand for sensitive optical detection methods which can be used in fully automated analyzers appertaining to laboratory diagnosis has evolved in recent years.

In addition to the requirements made of the measurement method, such as sensitivity, resolution or dynamic range, the high degree of automation means that, in the same way, requirements are also made of the automated testing, setting and, if appropriate, readjustment of the parameters of the measurement method used. Therefore, quality control and validation measures must likewise be ensured by automated methods.

In the different methods of analysis, the testing and securing of valid results are characterized by varying degrees of difficulty. While testing is possible in absorption spectroscopy, for example by using officially calibrated standards, this is not possible for methods of scattered light spectroscopy. In the method of forward light scattering, in particular, which utilizes angles or angular ranges near the incident beam of the light source, simultaneous measurement of characteristic optical parameters within the beam path is difficult on account of the mechanical structure. Therefore, characteristic optical parameters, such as intensity, wavelength, pulse length or noise component of the light source used, and with the use of a vessel (cuvette or the like) which serves to accommodate the material to be measured and is briefly inserted into the beam path, can frequently be determined only with the aid of an additional relative standard. However, the necessity of using nonstandardized test media gives rise to further fault sources which do not allow control over a relatively long period of time in situ and do not allow an unambiguous conclusion to be drawn about the property of the instrumental conditions.

In scattered light apparatuses, high-purity solutions 5 such as toluene, for example, are used in the majority of cases for reference measurements. Measurement of the angle-dependent scattered light characteristic produces a profile and thus a measure of quality for the apparatus used.

The use of such liquids is problematic for reasons of safety and, in addition, carrying out the measurements described above is time-intensive and complicated in terms of laboratory technology. For these reasons, these methods cannot be used for application in automated analyzers. However, if a corresponding material to be measured which generates scattered light is not present, no measurement signal can be generated and thus no conclusion can be drawn about the quality of the method under the current operating conditions.

Consequently, if a material to be measured which generates scattered light is used, then it will generate a signal which differs from measurement to measurement, depending on its composition, its structure and the procedure for its use. Simultaneous validation of the measurement system is thus precluded. These considerations also apply in a similar manner to methods in which the measurement signals are generated initially within the material to be measured, such as, for example, in the case of fluorescence or chemiluminescence reactions.

In the arrangement used most for scattered light measurement, the scattered light is detected under an angular range around 90° with respect to the direction of the incident beam. Separation of the incident light from the scattered light is particularly easy to achieve as a result. Alternatively, choosing a larger solid-angle range and utilizing angles or angular ranges around the forward direction of the incident light make it possible to achieve higher intensities of the scattered light, as a result of which an arrangement can be constructed in a technically simpler and more cost-effective manner. The proportion of scattered light at angles around the forward direction is particularly high precisely for the measurements (which are striven for in accordance with the present description) on organic macromolecules for use in human in-vitro diagnosis. In addition, use is made of the effect of increasing the intensity of the scattered light by the principle of particle enhancement. The dependence of the scatter signal on the particle size is the most favorable for the case in which the scattering particles are of an order of magnitude which corresponds to the order of magnitude of the wavelength of the incident light. This produces a preferred arrangement which makes it possible to utilize these components for the measurement. Fundamental considerations and calculations concerning the theory of scattered light are contained in the appropriate textbooks. The following may be mentioned here by way of example: H. C. van de Hulst (Light Scattering by Small Particles, Dover Publications, Inc. New York, 1957, 1981) and C. F. Bohren, D. R. Huffman (Absorption and Scattering of Light by Small Particles, J. Wiley & Sons, New York, 1983). Given further knowledge of the properties of the material to be measured which is to be examined, discrimination of the material to be measured into magnitude classes can be achieved by selection of one or more angular ranges.

The apparatuses used in automated laboratory diagnosis are frequently constructed from, these being known per se to a person skilled in the art, movable units (e.g. rack, carousel, rotor or the like) for accommodating a multiplicity of vessels for sample or reagent liquids and the vessels for accommodating and passing through the material to be measured (cuvettes). In the event of using a rotatable unit for the positioning of the material to be measured, the cuvettes, in dependence on their requirements imposed on the measurement recording, are guided cyclically past a stationary position of the measurement unit. When scattered light measurements are carried out, the resultant scattered light is produced by the material to be measured in a cuvette, said material being introduced into the beam path. This means that changes can be produced by different positioning of the material to be measured.

SUMMARY OF THE INVENTION

The object of the present invention is to find a method which makes it possible to control the properties of a method for measuring forward light scattering without the necessary use of a material to be measured which produces scattered light.

It has now been found that this object is achieved by means of an arrangement of the measurement unit in which the directly transmitted light is measured by a suitable detection device and, at the same time, the scattered light that is produced is detected.

For this purpose, a structure has been developed which makes it possible to measure the scattered light produced under angles not including 0° and the light transmitted under angles around 0°.

In particular, one aim of the method described is to carry out the control and validation of the beam path and the components used, such as the light source, the optical components of lenses and diaphragms and the properties brought about by the moving accommodating vessels of the material to be measured (cuvettes). Testing and control are likewise possible for the cuvette, which is situated in the beam path only during a measurement interval.

The arrangement described according to the invention can consequently be used as in-process control in automated analysis.

BRIEF DESCRIPTION OF THE DRAWINGS

The arrangement of the apparatus according to the invention is elucidated with reference to the following figures.

DETAILED DESCRIPTION OF THE PREFERRED EMBODIMENT

Figure 1:
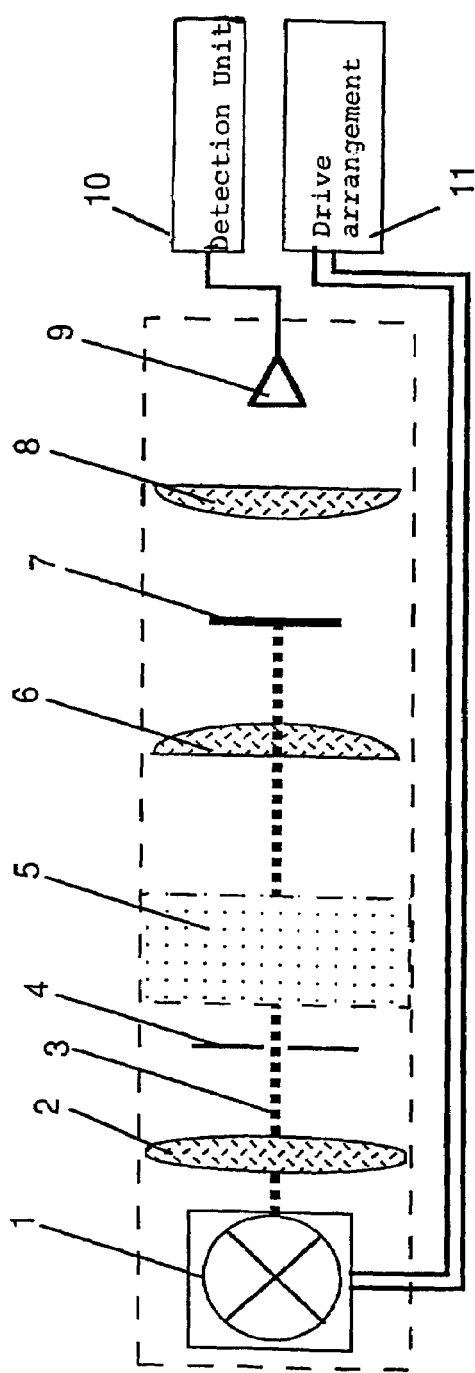
FIG. 1 is a side view of a structure used according to the principle of previous analysis methods.

FIG. 1 diagrammatically shows the principle of the previous method: a light beam 3 emerging from a light source 1, 11 passes through a lens system 2 and one or more diaphragms 4 to impinge on the measuring space 5; after passing through a lens system 6, the directly transmitted light from the light source 1 impinges on a diaphragm 7, which acts as a light trap. The light not extinguished by the diaphragm 7 is projected through a lens system 8 onto the detector 9 and measured by means of 10.

Figure 2:
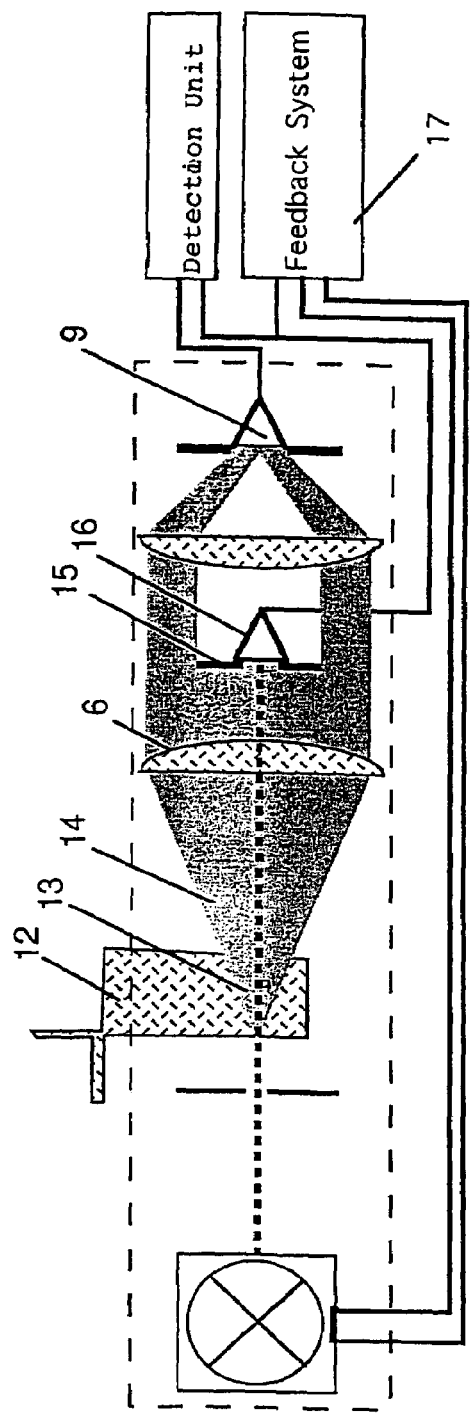
FIG. 2 is a side view of a structure for detection of the transmitted and scattered light according to the present invention.

FIG. 2 shows how the present invention augments the method. If, in accordance with FIG. 1, an accommodating vessel 12 with a material 13 to be measured which produces scattered light is positioned at the position 5, the measurement beam 3 penetrating said material to be measured, then a characteristic, angle-dependent scattered light distribution 14 is produced in dependence on the material to be measured. This distribution is detected by the aperture of the lens system 6 and 8 and passed to the detector 9. The light impinging on the region of the diaphragm 15 is detected by a further detector 16 and likewise measured. This component is composed of the component of the directly incident light from the light source and, given the presence of a material to be measured which produces scattered light, of the impinging scattered light fixed under the acceptance angle of the detector.

Controlling the position of the cuvette is advantageous for controlling the intensity of the scattered light produced by the material to be measured. This possibility is achieved according to the present invention by virtue of the independent control of the structure of the measurement unit (beam path) including the control of the type, structure and position of the cuvette without the use of a material to be measured which produces scattered light. The position thereby determined can be used for the synchronization of the measurement signal.

If the intention is to achieve a specific intensity at detector 16 for a cuvette 12, then this intensity can be detected and readjusted by measuring the intensity, without a material to be measured which produces scattered light, by means of the feedback system 17.

This affords the possibility of being able to carry out the scattered light measurements under relatively constant intensity conditions.

Figure 3:
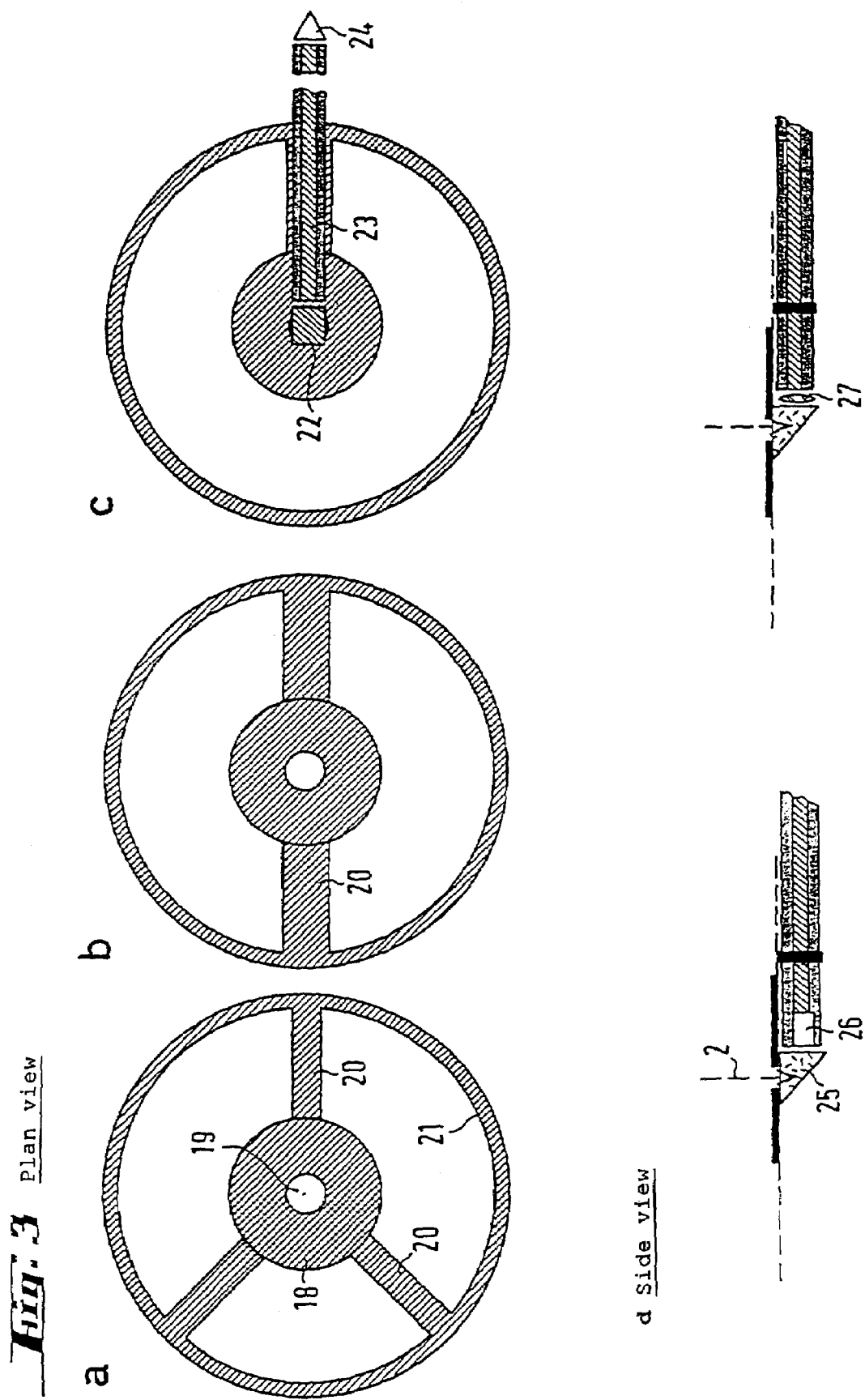
FIGS. 3A–C are plan views of alternative structure of the scattered light diaphragms according to the present invention.
FIGS. 3D–3E are side views of the light diaphragms shown in FIGS. 3A–3C.

Examples of possible configurations of the diaphragm 15 are shown in FIGS. 3A–C. The plan views in in FIGS. 3A–C comprise the diaphragm 15 with an outer holding ring 21, an annular diaphragm 18 and one or more webs 20 for retaining 18.

The inner diaphragm 18 is designed as a perforated screen for allowing the directly transmitted beam component to pass. It may have further mounts for beam deflection and launching of the light into a glass rod or optical waveguide 23 and a detector 24 situated at the end thereof.

FIGS. 3D and 3E show the diaphragm 15 in a side view. The measurement beam 2 is coupled into a light guidance unit 23 with the aid of a beam deflection arrangement 25 and a special optical arrangement 26, 27. The detection can be carried out in a manner locally separate from this unit.

Figure 4:
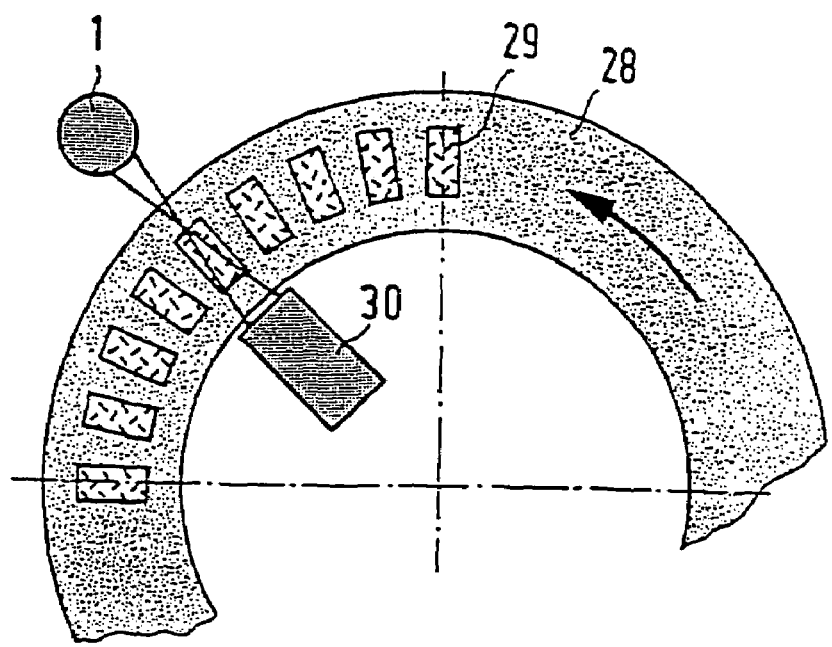
FIG. 4 is a top view of the position of the detection unit within a cuvette wheel according to the present invention.

FIG. 4 diagrammatically shows the incorporation of a detection unit within a rotatable mount (rotor system) 28 for accommodating the cuvettes 29. When the rotor rotates through the positions 1, 30, cyclic measurement is effected, the interval of this measurement being fixed by the speed parameter of the rotor. In the case of the measurement principle according to FIG. 1, a signal can be measured and evaluated only when the cuvette contains a material to be measured which produces scattered light.

Figure 5:
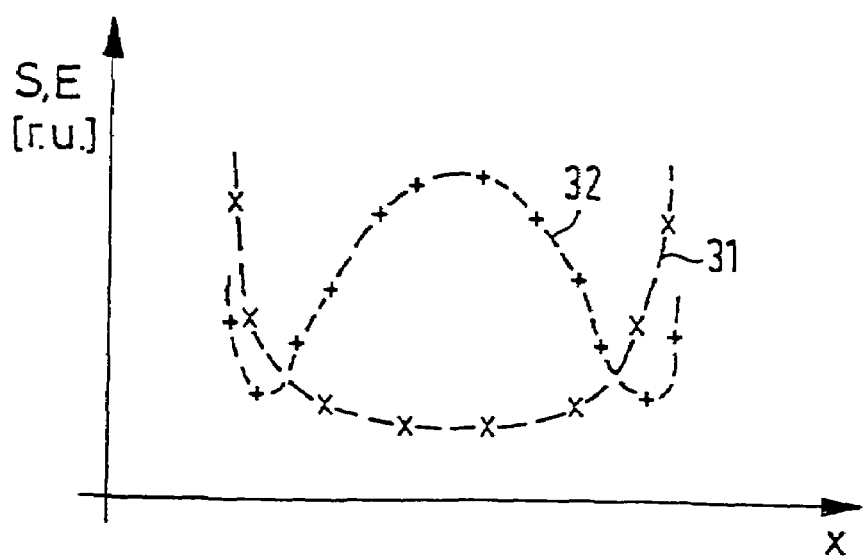
FIG. 5 is a diagrammatic representation of the intensity of the scattered M and transmitted (E) signal as a function of the cuvette position (x).

FIG. 5 represents the fundamental profile of the signals generated by extinction E or scattering S as a function of the cuvette position. In this case, the type, composition and position of the cuvette have a major influence on the level and waveform of the measurement signal. While the scattered light curve 32 can be produced only with a corresponding material to be measured, the curve of the component E produced by extinction can be measured even with cuvettes which are empty or filled with a non-scattering material to be measured, whereby independent determination of the position can be achieved.

The method according to the invention is of fundamental importance and can be used for any scattered light measurement. The scattered light measurement of biological macromolecules for determining concentration in the so-called nephelometric method is of particular importance.

The invention claimed is:

1. A method of obtaining a relatively consistent scattered light measurement, comprising:
    moving an accommodation vessel through a light beam via a rotor system;
    directing the light beam passing through the accommodation vessel toward a detection unit to produce a scattered component and a transmitted component of the light beam;
    cyclically measuring, via a first detector, an intensity of the transmitted component of the light beam based on a position of the accommodation vessel relative to the light beam;
    cyclically measuring, via second detector, an intensity of the scattered component of the light beam separately from the transmitted component based on the position of the accommodation vessel relative to the light beam;
    adjusting an intensity of the light beam directed through the accommodation vessel based on the measured intensity of the transmitted component of the light beam; and
    allowing the scattered component of the light beam to pass around a diaphragm upon which the transmitted component of the light beam impinges.

2. The method of claim 1, wherein the intensity of the transmitted component of the light beam is measured by a detector mounted on the diaphragm.

3. The method of claim 1, further comprising passing the transmitted component and the scattered component of the light beam through a first lens system.

4. The method of claim 1, further comprising passing the scattered component of the light beam through a second lens system.

5. The method of claim 1, further comprising separating the transmitted component of the light beam from the scattered component of the optical beam with a shaped diaphragm.

6. The method of claim 1, wherein the diaphragm includes a region for mounting a detector.

7. The method of claim 1, wherein the diaphragm includes a region for mounting a beam guidance or deflection unit.

8. The method of claim 1, further comprising separating the transmitted component of the light beam from the scattered component of the light beam by a mirror placed in a path of the light beam, a beam guidance or deflection unit mounted on a mounting region of the mirror.

9. The method of claim 1, further comprising separating the transmitted component of the light beam from the scattered component of the light beam by a machined lens placed in a path of the light beam, a beam guidance or deflection unit mounted on a mounting region of the lens.

10. The method of claim 1, wherein the step of measuring the intensity of the transmitted component of the light beam includes measuring the intensity with a detector having wavelength-selective components.

11. The method of claim 1, wherein signals of both the scattered and transmitted components of the light beam are measured both separately and simultaneously.

12. The method of claim 1, further including recording a signal of the transmitted component of the light beam as it passes through a vessel for accommodating a material to be measured as a function of a position of the vessel.

13. The method of claim 12, wherein the vessel is a cuvette.

14. The method of claim 1, further including setting, testing, and if appropriate, correction of the position of a vessel for accommodating a material to be measured, wherein the setting, testing, and correction includes moving the vessel through the light beam; scanning the vessel during its movement through the light beam; and recording a signal of the transmitted component of the light beam as a function of the vessel in order to define the position of the vessel relative to the light beam.

15. The method of claim 14, wherein the vessel is a cuvette.

16. The method of claim 1, wherein the method is used for in-process control for the purpose of validation in automatic diagnostic analyzers.

17. The method of claim 1, wherein the method is used in analysis processes.

18. The method of claim 1, wherein the method is used in in-vitro diagnosis processes.

19. The method of claim 1, wherein the first detector is positioned between the accommodation vessel and the second detector and the diaphragm is positioned between the first detector and the accommodation vessel.

20. A method of calibrating a system for measuring a specimen using light, comprising:
    directing a measuring light beam toward a detection unit;
    passing an empty vessel for accommodating a material to be measured through the path of the measuring light beam via a rotor system;
    separating a transmitted component of the measuring light beam from a scattered component of the measuring light beam;
    measuring the intensity of a transmitted component of the light beam based on a position of the empty vessel relative to the light beam;
    measuring the intensity of a scattered component of the light beam separately from the transmitted component based on the position of the empty vessel relative to the light beam;
    adjusting an intensity of the light beam based on the measured intensity of the transmitted component of the light beam; and
    allowing the scattered component of the light beam to pass around a diaphragm upon which the transmitted component of the light beam impinges.

21. The method of claim 20, wherein the method is used in analysis processes.

22. The method of claim 20, wherein the method is used in in-vitro diagnosis processes.

23. The method of claim 20, wherein the first detector is positioned between the empty vessel and the second detector and the diaphragm is positioned between the first detector and the empty vessel.

24. A method of measuring a specimen using light, comprising:
    calibrating a measuring system by:
        directing a measuring light beam toward a detection unit;
        passing an empty vessel for accommodating a material to be measured through the path of the measuring light beam via a rotor system;
        separating a transmitted component of the measuring light beam from a scattered component of the measuring light beam;
        measuring the intensity of a transmitted component of the light beam based on a position of the empty vessel relative to the light beam;
        measuring the intensity of a scattered component of the light beam separately from the transmitted component based on the position of the empty vessel relative to the light beam;

adjusting an intensity of the measuring light based on the measured intensity of the transmitted component of the light beam; and allowing the scattered component of the light beam to pass around a diaphragm upon which the transmitted component of the light beam impinges;

filling the empty vessel with the specimen to be measured;

placing the vessel containing the specimen to be measured in the path of the measuring light beam;

measuring the intensity of a transmitted component of the light beam; and measuring the intensity of a scattered component of the light beam separately from the transmitted component.

25. The method of claim 24, wherein the method is used in analysis processes.

26. The method of claim 24, wherein the method is used in in-vitro diagnosis processes.

27. The method of claim 24, wherein the first detector is positioned between the empty vessel and the second detector and the diaphragm is positioned between the first detector and the empty vessel.

* * * * *